United States Patent [19]

Friemel et al.

[11] Patent Number: 4,597,218
[45] Date of Patent: Jul. 1, 1986

[54] SACHET FOR USE IN PEST CONTROL

[75] Inventors: Wolfgang Friemel, Heppenheim; Reiner Ehret, Weinheim, both of Fed. Rep. of Germany

[73] Assignee: Dr. Werner Freyberg, Laudenbach, Fed. Rep. of Germany

[21] Appl. No.: 631,139

[22] Filed: Jul. 16, 1984

[30] Foreign Application Priority Data

Jul. 18, 1983 [DE] Fed. Rep. of Germany ....... 3325826

[51] Int. Cl.[4] ........................................... A01M 13/00
[52] U.S. Cl. ...................................... 43/131; 43/125; 428/35; 428/36; 428/76; 428/198; 428/288; 428/290; 428/302; 428/303; 428/311.5; 428/339
[58] Field of Search ................... 43/131, 125; 428/35, 428/36, 76, 198, 288, 290, 302, 303, 339, 311.5

[56] References Cited

U.S. PATENT DOCUMENTS

| 1,077,835 | 11/1913 | Kelly | 43/131 |
|---|---|---|---|
| 2,139,040 | 12/1938 | Salfisberg | 43/131 |
| 3,132,067 | 5/1964 | Rauscher et al. | 43/131 |
| 4,131,704 | 12/1978 | Erickson et al. | 428/296 |
| 4,199,548 | 4/1980 | Kaiho et al. | 43/125 |
| 4,215,508 | 8/1980 | Allen | 43/131 |
| 4,477,516 | 10/1984 | Sugihara et al. | 428/296 |
| 4,479,999 | 10/1984 | Buckley et al. | 428/296 |
| 4,485,133 | 11/1984 | Ohtsuka | 428/35 |
| 4,487,791 | 12/1984 | Komatsu et al. | 428/35 |
| 4,488,924 | 12/1984 | Krieg | 428/35 |

FOREIGN PATENT DOCUMENTS 1096519 2/1955 France .
2037769 12/1970 France .

Primary Examiner—James C. Cannon
Attorney, Agent, or Firm—Millen & White

[57] ABSTRACT

The invention relates to a sachet for pest control, composed at least in part of a gas- and water vapor-permeable substantially anhydrous non-woven fabric, said fabric being a plural component non-woven fabric comprising at least one material-forming fibers and having a melting or softening temperature above 165° C. and a second material having thermoplastic properties ad a melting or softening temperature below 145° C. The invention also relates to the use of the sachets for accommodating gas releasing pest control agents, in particular a composition based on alkaline earth and/or earth metal phosphides releasing phosphine gas.

44 Claims, 8 Drawing Figures

SACHET FOR USE IN PEST CONTROL

FIELD AND BACKGROUND OF THE INVENTION

The present invention relates to a sachet or small bag adapted for accommodating a gas-evolving pest control agent.

Solid pest control agents are known which when exposed to humid air will slowly release gaseous active substances. Such pest control agents may comprise hydrolyzable alkaline earth and/or earth metal phosphides, e.g. calcium phosphide, magnesium phosphide or aluminium phosphide, preferably aluminium phosphide, which are caused to release phosphine gas due to the moisture contained in the atmosphere or in a commodity to be fumigated. Such pest control agents are employed for example for the control of pests in stores or silos for grain, tobacco or other agricultural commodities, foodstuffs and luxury commodities. The pest control agent thus serves to eradicate animal organisms, for example bugs, beetles, moths, roaches or other insects or worms and even rodents such as mice and rats. In this context it is known to enclose such pest control agents into paper sachets which in use are introduced into the stored commodities. The pest control agent will then decompose slowly n the paper sachet and release its pest eradicating gaseous decomposition products through the walls of the sachet. The dust-like residues of the pest control agent on the other hand are to be retained by the paper sachet. The paper used for this purpose has to comply with special requirements regarding strength, gas permeability and water repellent properties.

However, such paper can be processed only within limits by automatic equipment (such as for example edge-sealing bag-forming machines, tubular bag-forming machines etc.) In general they are closed by sewing which is a labour-intensive operation. It may also happen that the sewing seams come loose and the poisonous contents then enter into the commodities to be treated.

A sachet for the accommodation of phosphine-evolving pest control agents is known also, composed of a gas pervious non-woven fabric of which the mesh openings are of predetermined dimensions. Materials mentioned for such non-woven fabrics include those based on cellulose or certain synthetic polymers. It is also stated that the manufacture of the sachets may proceed from a continuous length of non-woven fabric, inter alia by welding with the application of heat and/or ultrasonics. The aforegoing offers the advantage that the manufacture of a welded seam is less labor-intensive than the interconnecting of the layers of non-woven material or the various sides of such materials by adhesive action or sewing.

However, it was found that there is a need for improvement with regard to the welding and sealing properties of the non-woven fabrics used for the known sachets. In practice this applies both to the formation of a welding seam as such, as well as with regard to its strength and reliability when the sachets filled with pest control agent are used.

There accordingly exists a need for the provision of a sachet made of a material which on the one hand provides the gas permeability required in use, but which nevertheless retains the dust-like residues of the decomposed pest control agent, in addition to being very durable in character and being very suitable for being processed into a sachet of the desired properties by welding or sealing with heat and/or ultrasonics, preferably with heat.

To this end the present invention teaches inter alia that the sachet may be manufactured in a manner known per se from a special or specially selected non-woven fabric.

SUMMARY OF THE INVENTION

According to the invention, there is provided a sachet for pest control, composed at last in part of a gas and water vapor permeable substantially anhydrous non-woven fabric, said fabric being a plural component non-woven fabric comprising at least one material-forming fibers and having a melting or softening temperature above 165° C. and a second material having thermoplastic properties and a melting or softening temperature below 145° C.

DETAILED DISCUSSION

In the present specification the term "sachet" is used to denote a relatively small bag or envelope-like packet. The term is generally used in the pest control art. The term non-woven fabric is used to denote a fleece-like structure comprising more or less randomly orientated fibers.

According to preferred embodiments of the present invention, the fiber-forming material has a melting or softening temperature in the range from 180° to 235° C., whereas the second material preferably has a melting or softening temperature in the range from 80° to 120° C. In respect of materials which do not have a definite melting or softening point, the parameters stated above and in the claims apply mutatis mutandis to a corresponding melting or softening range.

It is thus an essential feature of the present invention that for the manufacture of the sachet according to the invention a non-woven fabric composed of a plurality of components is used. One such component is a material which forms fibers having a relatively high melting or softening temperature. Such materials which are suitable for the manufacture of non-woven fabrics are known in considerable variety and are in part already commercially available. Particular examples for this component include polyamides, polyesters, polyacrylic compounds, in particular polyacrylic amide and even glass fibers. In the case of high throughput machines it is possible even to employ polypropylene of relatively high softening temperature as the high melting component, for example in combination with polyethylene to serve as the lower melting component.

The second material having thermoplastic properties and used as the further component may be present in a variety of forms. According to a particular embodiment, this component also forms fibers which for example have a length of 0.5 to 1 mm.

However, it is also possible for this second component to be applied onto the fibers of the material having the higher melting or softening temperature in a manner known per se. This is possible for example by way of the sintering process described below:

The material which is used for the application by sintering is first ground to a fine powder in an intensely cooled suitable milling plant. This powder is then applied as uniformly as possible by means of application rate controlling rollers onto the non-woven fabric passing these rollers. The fabric then passes infra-red radiators of suitable temperature, thereby to subject the coating particles to incipient melting to cause adhesion. Optionally a calendering stage may follow, whereby the adhering particles are flattened somewhat and fixed even more thoroughly.

An alternative method of applying the second component onto the fiber-forming material comprises printing the second component onto the inner face of the fabric layer. Such application of the second material may also take place in the form of a solution or suspension of the respective thermoplastic material.

The application of the second material or a further material may serve wholly or predominantly to assist in the formation of the welding seams or also to modify the gas permeability and/or the dust-proofness of the non-woven fabric. Such application may be carried out over the entire surface area of the fabric or only selected parts thereof, namely the regions which are to be occupied by the welding seams. For reasons of reliability, the width of such zones of application of the second component onto the non-woven fabric where a welding seam is subsequently to be provided should be at least 1 cm, e.g. from 1 to 3 cm, more particularly from 1 to 2 cm.

Suitable substances to serve as the lower melting component of the non-woven fabric include in particular polyethylene and suitably selected polypropylene materials or copolymers of ethylene, propylene or butylene with vinyl acetate. A person skilled in the art may select suitable materials for this purpose.

In those particular embodiments of the invention in which the second component as well is present in the form of separate fibres, the fiber length of the higher melting component preferably exceeds that of the lower melting component, the former being for example from 5 to 20 mm and the latter preferably from 0.5 to 1 mm.

The result is that in the sachets according to the invention the interstices between the long fibers of the higher melting component are occupied by the lower melting component in the form of the shorter fibers which will then improve substantially the desired dust-proofness of the sachets according to the invention.

The mass ratio between the two aforesaid components is variable within relatively wide limits. Thus according to a particular embodiment of the invention, proportions of the higher melting component of 50 to 70% by mass (weight)—based on the total amount of higher melting component and lower melting component—are employed successfully.

However, it is also possible to use as the material for the non-woven fabric for the manufacture of the sachet according to the invention suitable dual component fibers, more particularly so-called coated core fibres. In that case the fibre-forming material provides the core, whereas the second material forms the outer layer. An example of such dual component fibers are those in which the core is composed of polyamide 6.6 and the outer layer of polyamide 6.

The porosity of the non-woven fabrics used according to the invention is such that on the one hand gases may pass therethrough quite easily, whereas the passage therethrough of dusts such as are formed by the hydrolysis of the pest control agent is blocked. Pore sizes of the non-woven fabric exceeding 2 $\mu$m, in particular of 5 to 15 $\mu$m, preferably between 10 and 12 $\mu$m have been found to satisfy this requirement. With such pore sizes virtually no residues of the pest control agent escape from the sachet according to the invention.

The manufacture of the non-woven fabrics employed for the sachet manufacture according to the invention may proceed according to processes which are well-known. For that reason it is considered adequate to state in this context only a few important principles.

More particularly, the non-woven fabrics comprising different fibers, used according to the invention may in principle be processed as follows and comprise the following materials:

carding webs for the manufacture of which the fiber on a card is laid out either parallel in the direction of movement or by a cross application means in zig-zag fashion onto a belt moving in a direction transverse to the card, aerodynamic non-woven fabrics for the manufacture of which loose fibers are blown by an airflow onto a sieve belt or onto a sieve drum to form a tangled fabric, or spun fabrics in the manufacture of which a suitable polymer, e.g. in the form of a granulate is melted and is withdrawn by a hot air current from a pivotally arranged spinneret with as much stretching as possible.

However, hydrodynamically produced non-woven fabrics are preferred according to the invention, these in accordance with a preferred embodiment being manufactured as follows:

The fibers of the high melting component as well as those of the lower melting component, are suspended in suitable vessels (vats) in a relatively high bath liquor ratio of up to 5000 parts water to 1 part fiber. In order to avoid unevenness of the fabric being produced, it is advantageous to separate the fiber bundles as completely as possible up to the single fiber stage, the use of a surfactant in the aqueous medium being advantageous. Because of the relatively large amounts of water, the use of an inclined sieve and of suction boxes underneath the inclined sieve is advantageous.

After the fibrous fabric has been formed, it is preferably subjected to a bonding procedure and optionally to an upgrading treatment.

In principle three different methods are available for the bonding procedure, namely mechanical bonding (for example by needle felting techniques or with the aid of water jets), chemical bonding and thermal bonding. For hydrodynamically deposited fabrics, chemical bonding is the most suitable of these three methods, the fibers of the non-woven fabric being adhesively bonded together by means of a binder. Such a binder is applied preferably in an amount of 15 to 50%, e.g. 20 to 30%, for example 20% by weight (based on the final mass of the fabric). Binders known per se based on caoutchouc or synthetic resins, such as polyacrylic acid esters or polyvinylchloride, polyvinylacetate or polyurethane are very suitable. It stands to reason that suitable mixed polymers such as for example copolymers of vinyl acetate with acrylic acid or methacrylic esters or with polyolefins, e.g. polyethylene can be used successfully. Suitable polyolefins may also be used. Advantageously appropriate dispersions of such synthetic resins are employed.

The binder used may be added at least in part to the fiber suspension and/or be applied onto the fabric in various manners, for example the following methods being usable:

An inpregnation in which the fabric is passed through a binder bath being soaked thereby followed by squeezing between two rollers and subsequent drying;

A spray process in which the fibrous fabric is sprayed while passing on a transport screen underneath spraying nozzles which may optionally be moved back and forth;

The application of a foam, the fabric being soaked with the foamed binder, but preferably not followed by subsequent pressing; and The Pflatsch process in which the binder by way of a revolving roller is wiped onto the fabric, the fabric receiving a binder application on one side only, and finally the application of the binder by means of pressure rollers.

After the application of the binder but also at any other stage of the process where a drying of the non-woven fabric is necessary or desirable, this may be carried out for example by means of infra-red radiators or preferably with driers employing air passing through the material.

Suitable upgrading methods include for example processes similar to those conventionally employed in textile finishing such as calendering, printing, dyeing, treatment with fire-proofing or fire retarding agents, etc. Such upgrading may proceed in an analogous manner and with the use of similar materials as those which have been known. In this context any dye content should not exceed 2 to 3% by mass of the overall composition. A dye may be incorporated also in the fiber-forming material or in the second material or in the fiber-bonding material, if present. Any one or more of these expedients are preferably resorted to so as to provide the sachets with a distinctive color readily recognized by the user and associated by the user with the source of origin and nature of the product. For example the same distinctive green colour is preferably employed which potential users are familiar with in the context of the prior art paper sachets.

In addition printed legends, printed trade mark matter (words, designs), warning notices and instructions for use may be applied by any suitable printing process.

The mass per unit of surface area of the non-woven fabric so produced is preferably between 50 and 120 g/m$^2$, the upper limit being determined inter alia by the reduction of the required flexibility of the material. According to a particular embodiment of the invention, the mass per unit of area of the non-woven fabric is about 70 g/m$^2$. In accordance with a particular embodiment of the sachet according to the invention coating of the non-woven fabric with a suitable plastics, for example polyethylene is provided for. Such coating may be applied e.g. in an amount of from 15 to 50 g/m$^2$, in particular 20 to 30 g/m$^2$, e.g. 20 g/m$^2$. The methods employed for such coating are known (e.g. sinter application). In manufacturing the sachet according to the invention, non-woven fabric taken from a continuous length of such fabric may be folded appropriately and be welded along the longitudinal sides. The solid pest control agent which is generally granulated may then be introduced through the remaining opening. Thereafter the remaining opening is closed as well. Another possibility provides for the sachet to be manufactured on an automatic tubular bag machine in a manner known per se with simultaneous filling. Obviously it is generally particularly advantageous to employ for the manufacture and/or the filling of the sachets according to the invention such apparatus as are already commercially available in various forms. Thus suitable automatic machines are available, for example on the basis of thermal welding or welding with ultrasonics (e.g. of the edge-sealing type). Suitable dimensions of the sachets according to the invention are obviously dictated by the desired quantities of pest control agents to be accommodated. After the closing of the sachet according to the invention, the pest control agent is enclosed completely and the dusts which are formed during its decomposition can no longer escape from the sachet. Accordingly, the sachet including the pest control agent can be added directly to the foodstuffs to be fumigated or other commodities. The production of the sachets by edge sealing may be carried out as follows: A continuous length of the non-woven fabric is first cut into two narrower lengths which are preferably of the same dimensions and arranged one above the other so as to face each other. They are passed to the welding step. Thereupon a U-shaped structure is welded by mean of two vertical and one horizontal sealing tools. Alternatively, one single U-shaped tool may be employed. The structure forms an empty sachet which is open at its top ready to be filled with the pest control composition. In the next cycle the lengths of the non-woven fabric move downward and again a U-shaped structure is produced. Preferably the horizontal sealing tool thereby concurrently seals the previously filled last sachet besides forming the new structure. It is also possible for two sealing tools to be positioned side by side, whereby two sachets which may be connected in the middle portion are formed.

By cutting the fabric horizontally, e.g. after 50 (double) welding and cutting cycles, a blanket having 100 sachets in two rows adjacent to each other is obtained.

It is obvious that, e.g. by cutting after each cycle in vertical direction and by cutting horizontally after 10 cycles two chains with 10 sachets each are formed. By cuttng both in horizontal and vertical direction after each cycle, two single sachets result.

The invention is also applicable to multiple sachets or sachets comprising several pockets. In this context intermediate seams formed e.g. by heat or ultrasonics serve to subdivide the sachets into pockets or segments. Double sachets may for example comprise a common transverse seam between the longitudinal sides. According to a particular embodiment of the present invention a plurality of the sachets according to the invention are connected as part of a large surface structure of larger dimensions than the individual sachets. The interconnection may be provided in any suitable form, for example adhesively or even by welding by the effect of heat or ultrasonics. The large surface structure can be composed of flexible material e.g. in the form of a sheet or foil and may take the form of an elongate belt, for example of a suitable plastics material such as a polyolefin and mixed polymers thereof, polyesters, mixtures of polyolefins(s) and polyester(s) or even modified non-hygroscopic cellulose material. There then exists a possibility of a very rapid and simple manner of spreading out the sachets. It is merely necessary to fix one end of this belt to an elevated locality and to allow the belt to unroll or unfold itself in any suitable manner, e.g. by gravity, whereafter each sachet is exposed to the atmosphere of the silo, the store building, the transport means etc. In this context reference is made to PCT application DE No. 79/00061, contents of which by reference thereto are to be considered part of the present disclosure. Substantially corresponding disclosures which may be applied in an analogous fashion occur in UK Pat. No. 2 0465 77, Australian Pat. No. 528 417, South African Pat. No. 79/2263, U.S. Pat. No.

4,215,508 and numerous other corresponding patents and patent applications.

If the belt is made of the same or a similar non-woven fabric as the sachets according to the invention it is also possible for such belt to form an integral part of the sachet by constituting one or both walls of a sachet. In a particular preferred embodiment a single non-woven fabric may be used for the belt as well as the individual sachets.

A further aspect of the invention comprises the use of a sachet as described in the aforegoing for accommodating a pest control agent adapted to deliver a gas, in particular a composition on the basis of alkaline earth and/or earth metal phospides adapted to evolve phosphine gas, more particularly calcium phosphide, magnesium phosphide or aluminium phosphide, the latter being preferred.

An advantage of the sachet according to the invention resides in its property of virtually complete gas permeability, combined with its ability to retain the pest control agent even when decomposed. A sachet according to the invention adapted to accommodate a pest control agent moreover has improved durability and an extremely low moisture content. The result is that premature undesirable gas evolution during its manufacture can be avoided. It is moreover suitable for manufacture and filling by easy welding with the aid of heat or ultrasonics in commercial types of welding and packaging machines. The welding seams provide satisfactory closure and strength, such that no risk exists either during their manufacture, nor during the use of the sachets according to the invention for the intended purpose that the enclosed pest control agent or its residues may leak out. Accordingly, they can be considered particularly safe and reliable.

The sachets according to the invention whether in the form of individual sachets, multiple sachets or structures of large surface area, e.g. belts serve in practical use as a combined packaging and application means for a fumigant contained therein. They are filled with preferably accurately measured portions of the fumigant, closed by welding and are normally thereafter initially packed (individually or several sachets jointly) in a further gas and moisture-proof cover, e.g. a sealed cover of aluminium foil or a tin can or plastic can (e.g. metal-foil laminated) for storage and transport.

Since the sealing- or welding seams are generally stronger ad still more tear-resistant than the other parts of the sachets they are especially suitable to be provided with apertures, holes, metal eyelets etc. Through corresponding apertures or holes, e.g. a string can be passed which is advantageous in handling the sachets, belts etc. when they are taken out of any container and during their use including their removal after the development of the phosphine is completed.

The materials for the non-woven fabric of the sachets can easily be so selected that the sachets are chemically resistant to any chemical substances conventionally employed as additives in the fumigating compositions and in general the substances referred to above for the non-woven fabric and the treatment thereof have the required degree of resistance.

The specified selection of melting or softening temperatures of the materials, in particular the lower melting component is also of practical significance since it allows rapid formation of the welding seams without the application of excessive heat which might create high temperature conditions which might be harmful during the introduction of the pest control agent, e.g. by promoting decomposition of some heat-sensitive ingredients if present. Rapid welding also helps to minimize the time delay between the introduction of the pest control agent into the sachets and their subsequently being sealed into gastight containers. On the other hand the temperature limits specified allow the softening temperatures to be selected sufficiently high to avoid inadvertent opening of the sachets due to the generation of heat by any decomposition reaction of the pest control agent.

The sachets are to be so dimensioned in relation to the quantities of pest control agent to be accommodated therein, that they can absorb the volume increase of the solid residue of such compositions resulting from the hydrolysis reaction of the metal phosphide.

The following are typical examples of suitable dimensions for sachets according to the invention:

Single sachet

Internal side lengths from 5–10 cm by 7–15 cm, e.g. 8×10 cm, welded seam 5–10 mm, e.g. 8 mm.

Composite belts ("bag blankets") Total width, including welding seams (5–10 mm) 15–32 cm, e.g. 32 cm (2 integrated sachets side by side). Length 3–10 m, e.g. 5 m for 100 integrated sachets. Double transverse seams may be provided to permit the cutting off of a desired length.

Typically each sachet contains between 15 and 50 g, say 34 g pest control composition comprising from 5 to 15 g available (i.e. releasable) phosphine. 11.32 g available phosphine has become standard for aluminium phosphide compositions. In the case of a magnesium phosphide composition it is at present preferred to limit the individual portions to smaller amounts of available phosphine. Because of the high reactivity of magnesium phosphide the subdivision into smaller portions is safer. Also, because of the more rapid release of phosphine by magnesium phosphide it is sometimes possible to acheive the desired effect with lesser total amounts of available phosphine. Accordingly portions containing smaller available amounts of phosphine facilitate a more economical use of magnesium phosphide.

For improved protection of the pest control agent against accidental contact with liquid water it is possible to treat the fibers of the non-woven fabric or the completed sachet with a hydrophobising agent, e.g. in a manner known per se, e.g. with a suitable silicone compound, by spraying or impregnation.

DESCRIPTION OF SPECIFIC EMBODIMENTS WITH REFERENCE TO THE DRAWINGS

Although the invention should be readily understandable to those skilled in the art from the aforegoing detailed description, those features lending themselves to pictorial representations will be briefly described in the following with reference to the drawings which are not to scale. The description which now follows should be read in conjunction with the details of the aforegoing description.

Figure 1:
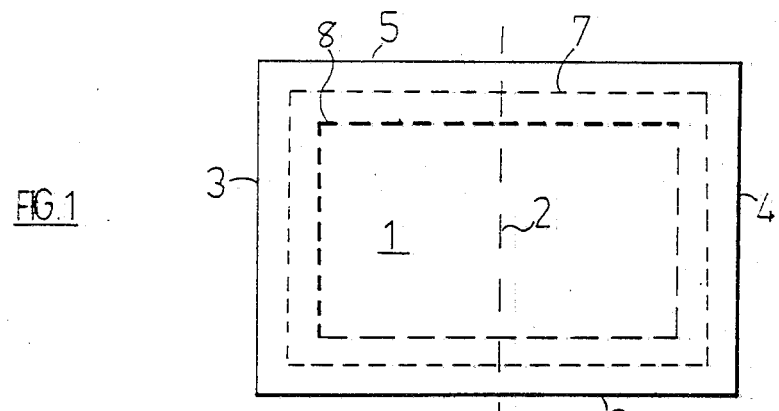
FIG. 1 represents a diagrammatic plan view of a sheet of non-woven fabric for making a single sachet according to the invention.

Referring first to FIG. 1, there is provided a sheet of vapour-permeable substantially anhydrous non-woven fabric 1 which as previously described comprises at least one material forming fibers and having a melting or softening temperature above 165° C. and optionally also a second material having thermoplastic properties and a melting or softening temperature below 145° C. The sheet has short sides 3 and 4 and long sides 5 and 6. In order to form a sachet according to the invention, the sheet is folded along the center line or folding line 2 so that short sides 3 and 4 become superimposed on one another. Welding seams are then produced by heat application or ultrasonics in the conventional manner between dotted outlines 7 and the outer peripheries (sides 3, 4, 5, 6 of the sheet), but leaving initially one side open. Pest control agent is introduced in a measured amount through the side left open, whereafter that side is similarly closed by heat or ultrasonic welding. It will be understood that if the device is formed by folding along line 2 it is not necessary to produce a welding seam along side 2, although this can be done if so desired. The application of the second material and/or a further thermoplastic material may be confined to a marginal region or zone indicated by broken line 8 and extending preferably beyond the outlines of the welding seam 7. The outlines 8 may be confined by the use of templates or masks, by the use of any suitable printing process, e.g. silk screening for applying the component selectively to certain regions. Furthermore, if the component is intended to enhance the formation of the welding seams, but a lighter application of the same component is desired to reduce the average pore size of the fabric, it is possible to apply a lighter application of that component inside the outlines 8 and a heavier application selectively between the outlines 7 and the sides 3, 4, 5, 6.

Referring still to FIG. 1, it is also possible to form a sachet according to the invention of twice the size described above by applying a second layer of non-woven fabric, e.g. identical to that described with reference to FIG. 1, face down, onto the sheet shown in FIG. 1. In that case all four sides 3, 4, 5 and 6 are closed by welding all round, one side being left open until the pest control agent has been introduced.

Figure 2:
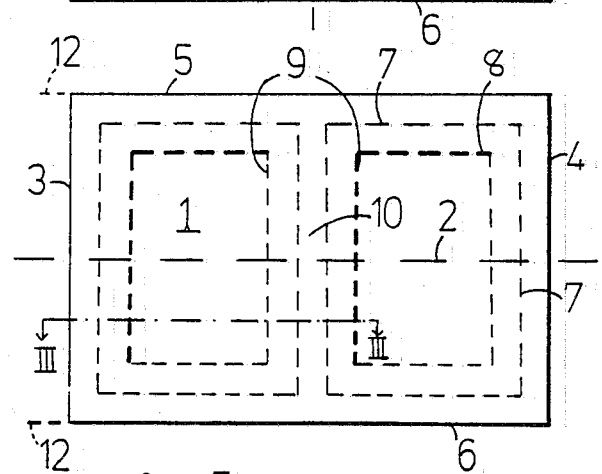
FIG. 2 represents a view similar to that of FIG. 1 of a sheet of non-woven fabric in the course of its being converted into a double or multiple sachet device according to the invention.
Figure 3:
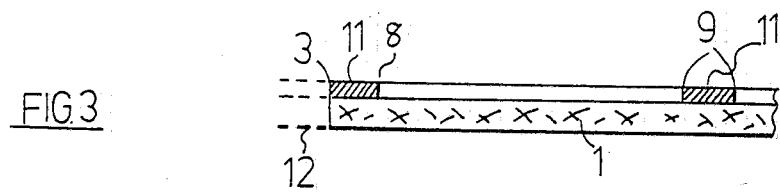
FIG. 3 represents a section along the line III—III in FIG. 2 on a different scale.

Referring to FIGS. 2 and 3, the same reference numbers have been used as in FIG. 1 to denote analogous integers. In contrast to the embodiment according to FIG. 1, the sheet of non-woven fabric 1 in this case is to be converted into a double sachet or multiple sachet comprising two or more pockets for holding pest control agents divided by transverse welding seams 10 formed in the zone 11 where the same measures as mentioned above regarding the marginal region or zone can be taken (outlined by outlines 9 and 3, 8 respectively). The dotted lines 12 in FIG. 2 are intended to indicate that the pattern of FIG. 2 can be repeated any number of times to provide for the desired number of pockets in multiple sachets in excess of the two pockets provided for in FIG. 2. Folding of the sheet 1 proceeds again along line 2 to produce multiple sachets which in plan view are half the size of the sheet.

As explained with reference to FIG. 1, it is possible instead of folding the sheet 1 as just described to apply a second sheet of non-woven fabric on top of sheet 1 followed by welding to produce multiple sachets double the size just described.

Figure 4:
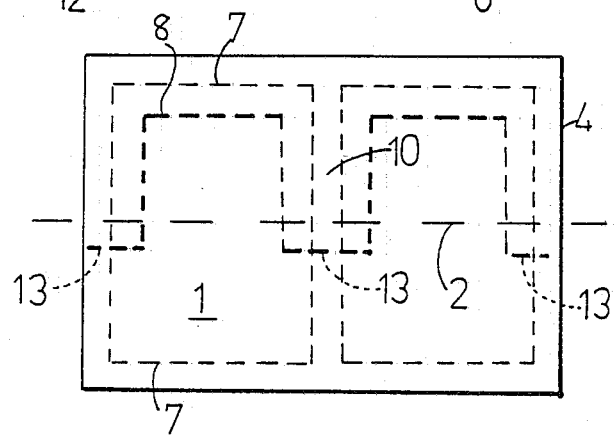
FIG. 4 represents a view similar to that of FIG. 2 to illustrate a modification thereof and of the method of manufacturing sachets according to the invention.

Referring now to FIG. 4, when the sachets are to be formed by folding the sheet 1 along folding lines 2, a coating need only be provided on one side of the folding line 2, e.g. as indicated by the outline 8 terminating at 13.

It should be understood that what has been described with reference to FIGS. 1 to 4 in connection with sachets manufactured from single or double sheets of non-woven fabric can in practice be done using continuous lengths of such fabric on automatic machines where cutting of the non-woven fabric to the required lengths will normally take place only after the sachets have been formed.

Figure 5:
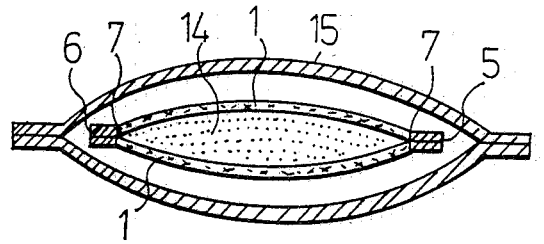
FIG. 5 represents a section through an embodiment of a packaged single sachet according to the invention.

Referrng now to FIG. 5, a single sachet is shown as described with reference to FIG. 1 composed of two layers of non-woven fabric 1, peripherally welded together in the regions 5, 7 and 6, 7 and filled with a pest control agent 14 in granule or powder form. One or more of these sachets are sealed in a gas-tight manner into strong envelopes 15, e.g. of heat weldable laminated aluminium foil. These envelopes serve to protect the sachets and the pest control agent 14 against exposure to atmospheric moisture. Immediately prior to use the envelopes 15 are torn or cut open without damaging the sachets. The sachet is removed and quickly placed into position in the commodity or space to be fumigated and after a while, when atmospheric moisture has penetrated through the non-woven fabric 1 into the pest control agent, hydrolysis will set in to release a gas (phospine) which escapes through the pores of the non-woven fabric 1 into the surrounding environment thereby to exercise its fumigating effect. Such hydrolysis is normally completed after a few days when the pest control agent by the hydrolysis reaction has been reduced to a loose powder which is trapped inside the sachet. The sachet thus prevents contamination of the commodity or environment with the powder. The powder has a bulk volume substantially larger than the bulk volume of the original pest control composition.

Figure 6:
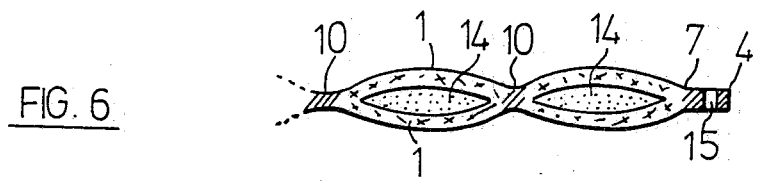
FIG. 6 represents a section through multiple sachets according to the invention.
Figure 7:
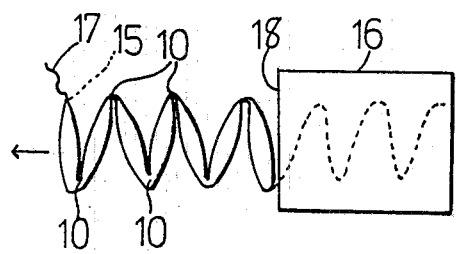
FIG. 7 represents a diagrammatic side elevation of one embodiment of a multiple sachet belt according to the invention in the process of its being withdrawn from its package.

Referring now to FIG. 6, a multiple sachet as described with reference to FIGS. 2, 3 and 4 is shown in section. The shaded areas 10 represent the welding seams which separate the individual sachet pockets filled with pest control agent 14. The last such welding seam between edge 4 and inner outlines 7, being a strong and relatively tear-resistant region has been provided with an aperture 15 for the attachment of the device, e.g. by means of a string passed through the hole 15. Optionally the hole 15 may accommodate a metal eyelet. Referring now to FIG. 7, a multiple sachet device is packed folded in concertina fashion in a gas-tight container 16. The concertina folds coincide with the transverse welding seams 10 between the individual sachet pockets described with reference e.g. to FIG. 6. The marginal welding seam at one end of the assembly has a hole 15 fitted with a fastening string 17. In FIG. 7 the container 16 has been opened on one side 18, through which the device is shown being withdrawn in the direction of the arrow.

Figure 8:
FIG. 8 represents a top view on a tin can (lid removed) containing an alternative embodiment of a multiple sachet device according to the present invention.

Referring now to FIG. 8, an alternative embodiment of a multiple sachet device 19 is shown composed of a large number, e.g. 100 individual sachets 20 interconnected via welding seams 10 to form a continuous belt-like device rolled up and accommodated inside the gas-tight tin can 21. Again one end of the device is fitted with a fastening string 17 as in FIG. 7.

What is claimed is:

1. A sachet for pest control, composed at least in part of a gas-permeable and water vapor-permeable substantially anhydrous non-woven fabric, said fabric being a plural component non-woven fabric comprising at least one material forming fibers and having a melting or softening temperature above 165° C. and a second material having thermoplastic properties and a melting or softening temperature below 145° C. and containing enclosed thereby a pest control agent adapted to release a pesticidal gas when the sachet is exposed to ambient atmosphere.

2. A sachet according to claim 1, wherein the fiber-forming material has a melting or softening temperature in the range from 180° to 235° C.

3. A sachet according to claim 1, wherein the second material has a melting or softening temperature in the range of from 80° to 120° C.

4. A sachet according to claim 1, wherein the second material is also present in the form of fibers.

5. A sachet according to claim 1, wherein the fiber-forming material includes a polyamide, polyester, polyacrylic resin, polypropylene having a relatively high softening temperature or glass fibers or a combination thereof.

6. A sachet according to claim 1, wherein the fiber length of the fiber-forming material is from 5 to 20 mm.

7. A sachet according to claim 1, wherein the second material comprises polyethylene, copolymers of ethylene, propylene, butylene and vinyl acetate or polypropylene having a relatively low softening temperature.

8. A sachet according to claim 4, wherein the fiber length of the second material is from 0.5 to 1 mm.

9. A sachet according to claim 1, wherein the fiber forming material and the second material are present in a mass ratio of from 50:50 to 70:30.

10. A sachet according to claim 1, wherein the non-woven fabric contains binder.

11. A sachet according to claim 10, wherein the fabric contains binder in an amount of 20 to 30 mass percent.

12. A sachet according to claim 10, wherein the binder is a polyacrylic acid ester, a copolymer of ethylene, propylene or butylene and vinyl acetate, polyvinylchloride or polyvinyl acetate, applied in the form of a dispersion or other suitable form, or a latex of natural or synthetic caoutchouc.

13. A sachet according to claim 1, wherein the non-woven fabric has welded seams therein and a coating of thermoplastic material on the non-woven fabric at least in the regions of the welded seams.

14. A sachet according to claim 13, wherein the thermoplastic material comprises polyethylene or polyethylene vinyl acetate copolymer.

15. A sachet according to claim 13, wherein the coating is present thereon in an amount of from 15 to 50 g/m$^2$.

16. A sachet according to claim 15, wherein the amount of the coating is from 20 to 30 g/m$^2$.

17. A sachet according to claim 1, wherein the plural component non-woven fabric comprises fibers of at least one of the fiber-forming materials onto at least part of the surface of which the second material has been applied.

18. A sachet according to claim 17, wherein the second material is polyethylene or ethylene/vinyl acetate copolymer.

19. A sachet according to claim 17, wherein the second material has been applied onto the first one by sintering or by printing or impregnation using a solution or emulsion of the second material.

20. A sachet according to claim 17, wherein the second material is present only in zones of the non-woven fabric bearing a welding seam.

21. A sachet according to claim 20, wherein the width of those zones is at least 1 cm.

22. A sachet according to claim 21, wherein the width of the zones is from 1 to 3 cm.

23. A sachet according to claim 22, wherein the width of the zones is from 1 to 2 cm.

24. A sachet according to claim 1, wherein the plural component non-woven fabric is composed at least in part of coated core bicomponent fibers, comprising a core formed by the fiber-forming material and a coating formed by the second material.

25. A sachet according to claim 24, wherein the core is composed of polyamide 6.6 and the coating is composed of polyamide 6.

26. A sachet according to claim 1, wherein the filaments of the non-woven fabric have a thickness from 1 to 20 dtex.

27. A sachet according to claim 26, wherein the thickness is from 1.5 to 3 dtex.

28. A sachet according to claim 27, wherein the thickness is from 1.7 to 2 dtex.

29. A sachet according to claim 1, wherein the non-woven fabric has a mass per surface area of from 50 to 120 g/m$^2$.

30. A sachet according to claim 1, formed of lengths of non-woven fabric welded together by heat and/or ultrasonics to form welded seams in the fabric.

31. A sachet according to claim 30, in the form of a tubular bag or a side-sealed bag.

32. A plurality of sachets according to claim 1 joined together to form a plurality of members of a flat composite structure.

33. Sachets according to claim 32, wherein the flat structure is flexible.

34. Sachets according to claim 33 wherein the flat structure is in the form of an elongate belt adapted to be rolled up or folded up concertina-like.

35. Sachets according to claim 34 wherein the belt is formed of the same material as that of the sachets.

36. Sachets according to claim 35, wherein the material forming the belt forms at least one side of the sachet.

37. A sachet according to claim 1, wherein the pest control agent is sealed therein by heat and/or ultrasonically welded seams in the fabric.

38. A claim according to claim 1, wherein the non-woven fabric is a tangled fiber web produced hydrodynamically.

39. A sachet according to claim 1 partly or wholly dyed and/or printed in a distinctive color.

40. A sachet according to claim 1, wherein the fibers of the non-woven fabric are hydrophobised with a hydrophobising agent.

41. A sachet according to claim 1, wherein the pest control agent comprises a phosphine-releasing material.

42. A sachet according to claim 1, wherein, the pest control agent comprises a phosphine releasing alkaline earth and/or an earth metal phosphide.

43. A sachet according to claim 1, wherein one or more of the sachets are sealed for transport or storage in a gas and moisture-proof envelope.

44. A sachet according to claim 1, wherein the pest control agent is sealed therein by heat and/or ultrasonically welded seams in the fabric;
- wherein the pest control agent comprises a phosphine-releasing material; and
- one or more of the sachets are sealed for transport or storage in a gas and moisture-proof envelope.

* * * * *